(12) United States Patent
Choi et al.

(10) Patent No.: US 10,888,533 B2
(45) Date of Patent: Jan. 12, 2021

(54) TRANSDERMAL COMPOSITION CONTAINING DONEPEZIL AS ACTIVE INGREDIENT

(71) Applicant: ICURE PHARMACEUTICAL INC., Seoul (KR)

(72) Inventors: Young Kweon Choi, Seoul (KR); Dong Hyun Hong, Jeollabuk-do (KR); Seong Soo Kim, Gyeonggi-do (KR)

(73) Assignee: ICURE PHARMACEUTICAL INC., Seoul (KR)

( * ) Notice: Subject to any disclaimer, the term of this patent is extended or adjusted under 35 U.S.C. 154(b) by 0 days.

(21) Appl. No.: 15/625,054

(22) Filed: Jun. 16, 2017

(65) Prior Publication Data

US 2017/0290780 A1 Oct. 12, 2017

Related U.S. Application Data (63) Continuation of application No. PCT/KR2015/013940, filed on Dec. 18, 2015.

(30) Foreign Application Priority Data

Dec. 18, 2014 (KR) .................. 10-2014-0183446

(51) Int. Cl.
- *A61K 9/70* (2006.01)
- *A61K 47/30* (2006.01)
- *A61K 31/445* (2006.01)
- *A61K 31/40* (2006.01)

(52) U.S. Cl.
CPC .............. *A61K 9/7084* (2013.01); *A61K 9/70* (2013.01); *A61K 31/445* (2013.01); *A61K 47/30* (2013.01); *A61K 31/40* (2013.01)

(58) Field of Classification Search
None
See application file for complete search history.

(56) References Cited

U.S. PATENT DOCUMENTS

| | | | | |
|---|---|---|---|---|
| 5,985,317 A | * | 11/1999 | Venkateshwaran | A61K 9/703 424/447 |
| 2004/0258741 A1 | | 12/2004 | Terahara et al. | |
| 2008/0131490 A1 | * | 6/2008 | Hanatani | A61K 9/7061 424/448 |
| 2009/0291127 A1 | | 11/2009 | Wen et al. | |
| 2010/0080842 A1 | * | 4/2010 | Wen | A61K 9/7061 424/448 |
| 2010/0178307 A1 | * | 7/2010 | Wen | A61K 9/7084 424/400 |
| 2010/0209484 A1 | * | 8/2010 | Choi | A61K 9/7038 424/449 |
| 2013/0095168 A1 | * | 4/2013 | Choi | A61K 9/7061 424/448 |
| 2013/0281542 A1 | * | 10/2013 | Valia | A61K 9/0014 514/654 |
| 2014/0052081 A1 | * | 2/2014 | Yang | A61K 31/445 604/307 |

FOREIGN PATENT DOCUMENTS

| | | |
|---|---|---|
| CN | 102895217 A | 1/2013 |
| CN | 104144684 A | 11/2014 |
| JP | 1999-315016 | 11/1999 |
| KR | 2005-0037405 | 4/2005 |
| KR | 2009-0101667 | 9/2009 |
| KR | 2012-0001844 A | 1/2012 |
| KR | 2013-0022602 | 3/2013 |
| KR | 2013-0098902 A | 9/2013 |
| WO | WO 02/069942 A1 | 3/2002 |
| WO | WO 2009120002 | * 10/2009 |
| WO | WO 2013/129813 A1 | 2/2013 |

OTHER PUBLICATIONS

International Search Report corresponding to Korean patent application No. PCT/KR2015/013940 dated Apr. 1, 2016.
English Translation of the IPRP and Written Opinion corresponding to Korean Patent Application No. PCT/KR2015/013940 dated Jun. 20, 2017.
Extended European Search Report corresponding to European Patent Application No. 15870365.2 dated Jul. 18, 2018.

* cited by examiner

*Primary Examiner* — Danah Al-Awadi
(74) *Attorney, Agent, or Firm* — Jenkins, Wilson, Taylor & Hunt, P.A.

(57) ABSTRACT

The present invention relates to a transdermal composition for dementia treatment containing donepezil as an active ingredient. The transdermal composition according to the present invention contains highly concentrated donepezil in a hydrophobic matrix, can continuously release the drug for a long time by having excellent long-term adhesion to the skin, and further exhibits consistently effective therapeutic effects over a long period of time by having a significantly improved skin penetration rate in comparison with conventional donepezil patches.

19 Claims, 2 Drawing Sheets

TRANSDERMAL COMPOSITION CONTAINING DONEPEZIL AS ACTIVE INGREDIENT

CROSS REFERENCE TO RELATED APPLICATIONS

The present application is a continuation of PCT Application No. PCT/KR2015/013940, filed Dec. 18, 2015, which claims priority from and the benefit of Korean Patent Application No. 10-2014-0183446 filed on Dec. 18, 2014, both of which are hereby incorporated by reference in their entireties.

TECHNICAL FIELD

The present invention relates to a transdermal composition comprising donepezil as an active ingredient and, more specifically, to a transdermal composition comprising donepezil as an active ingredient, the transdermal composition containing: (a) a backing layer; (b) a drug-containing matrix layer comprising, based on a total weight of the drug-containing matrix layer, (b-1) 15-55 wt % of donepezil or a pharmaceutically acceptable salt thereof, (b-2) 25-70 wt % of an EVA-based adhesive, (b-3) 5-20 wt % of at least one selected from the group consisting of a pyrrolidone derivative and a $C_{8-18}$ aliphatic derivative, and (b-4) 1-10 wt % of triacetin or a citric acid derivative, (c) a polymer adhesive matrix layer comprising, based on a total weight of the polymer adhesive matrix layer, 60 wt % or more of an acrylic adhesive; and (d) a release layer.

BACKGROUND ART

Dementia refers to a syndrome of complex cognitive impairment characterized by amnesia, degeneration of intelligence, changes in personality, behavioral abnormalities, and the like. These symptoms, which are those of degenerative brain nerve disease associated with the brain which is a part of the central nervous system, cause irreversible dysfunction in a neuron network due to the slow apoptosis of nerve cells, which causes degenerative diseases of the central nervous system, ultimately leading to permanent loss of corresponding body functions. The common feature of degenerative brain nerve diseases is the apoptosis of overall or specific cells. Since differentiated nerve cells do not possess regenerative potentials, the apoptosis of nerve cells causes the irreversible loss of brain functions.

It has not been fully established how dementia occurs, and there has been no dementia drug capable of being effectively administered alone since dementia has various pathologic and pathophysiological factors. However, it has been indirectly known that choline acetyltransferase (ChAT), which is involved in the synthesis of acetylcholine (ACh), is reduced by about 20-30% in the brain of demented patients compared with the brains of normal persons. It has also been known that the concentration of acetylcholine as a neurotransmitter is reduced by about 16-30%. Therefore, researches on the use of inhibitory agents suppressing cholinesterase (ChE), which is an enzyme hydrolyzing acetylcholine as a neurotransmitter, through an indirect therapeutic method have been conducted. Cholinesterase has two forms: acetylcholinesterase (AChE) and butylcholinesterase (BuChE). The above-mentioned acetylcholinesterase is an enzyme that hydrolyzes acetylcholine, which is one of the neurotransmitters mediating the activity of parasympathetic nerves in the body, into choline and acetate. Acetylcholinesterase is formed in endoplasmic reticulum membranes, and moves to cell membranes to perform its functions. The enzyme is the most widely distributed in cholinergic nerves and its surroundings, especially in muscle-nerve junctions, while being an important enzyme which is found in the plasma, the liver, and other tissues. Therefore, most of currently used therapeutic agents for Alzheimer's dementia are inhibitors of acetylcholinesterase, which is an acetylcholine degradation enzyme. These include donepezil (trade name: Aricept), tacrine (trade name: Cognex), rivastigmine (trade name: Exelon), and galantamine (trade name: Reminyl).

Donepezil, which is an acetylcholinesterase (AChE) inhibitor, is used for the treatment of dementia, such as Alzheimer's disease with a mild to severe degree or higher. In Alzheimer's disease, in association with which cholinergic nervous system disorders in the brain have been reported, AChE inhibitors, such as donepezil, increase acetylcholine in the brain to activate the cholinergic nerves in the brain. A donepezil composition, which is currently commonly used, is in the form of a tablet, and is prescribed to patients with Alzheimer's disease in the form of an oral preparation.

However, in general, the acetylcholinesterase inhibitor as an oral composition has serious side effects, and in particular, is reported to cause problems such as hepatic or digestive dysfunction or disorder. The cause of the side effect is that an oral composition cannot generally avoid an effect of the primary passage into the liver, and as a result, the oral composition easily affects liver functions. Also, the oral composition has high concentration in the digestive tract, and thus, side effects are likely to occur in the digestive tract. In addition, with respect to a change in the blood drug concentration after administration of an oral composition, the ratio of the maximum blood drug concentration reached after administration to the blood concentration 24 hours later (i.e., at the time of subsequent administration) is high, and thus, it is not easy to maintain a therapeutic effect over a long period of time, while the blood concentration does not reach a concentration at which side effects occur.

Therefore, Japanese Patent Application Laid-Open Publication No. 1999-315016 discloses that an oral administration may be difficult when the conditions of dementia are significantly advanced, and thus, a suppository for rectal administration and an ointment have been proposed to solve the problem. However, these dosage forms are problematic in that they are not practical for continuous administration of active ingredients over a long period of time.

In addition, US Patent Application Laid-Open Publication No. 20040258741 and Korean Patent Application Laid-Open Publication No. 2005-0037405 proposed a transdermal composition using synthetic rubber-based polymers of SIS and PIB bases. However, since its permeation rate is insufficient, and a transdermal composition having an area of 50 cm² or more must be applied for one or two days at a time, a long-term administration thereof imposes a heavy burden on the skin. In addition, the transdermal composition has a difficulty in containing a high concentration of a drug in a significantly hydrophobic matrix, and generates crystals at a concentration of 8% or more, causing a decrease in adhesive strength, non-uniformity of skin permeation rate, and storage problems. In addition, in order to allow a matrix to contain a drug having an amount necessary for satisfying the required dose, the thickness of the matrix needs to be increased proportionally to the amount of the drug, and therefore, the permeation rate of the drug does not change greatly at first, but is reduced over time.

Meanwhile, the present inventors have filed a patent application (Korean Patent Application Laid-Open Publication No. 2009-0101667) for a single-layer donepezil transdermal composition capable of minimizing side effects of the drug while facilitating compliance by a patient with dementia compared with an oral composition. However, the transdermal composition in the previous application has undesirable disadvantages for long-period adhesion (and dosing) of substantially more than one day, since such a transdermal composition contains a drug in a too low concentration to be administered for a long period of time; a patch containing the drug is thick; and an EVA adhesive constituting the drug-containing layer possesses a low adhesive strength even though the transdermal composition is administered as a system in which the drug-containing layer is in direct contact with the skin.

In addition, many conventional patches are provided in a form in which a desired drug is incorporated into a layer in direct contact with the skin for the purpose of increasing the amount of skin permeation of a drug. However, in this case, crystals are formed in such a layer over time, and thus such a patch causes lowered adhesive strength and changed physical properties, and is poorly released from a release film. There have been attempts to increase adhesive strength by placing a drug-containing layer and a separate adhesive layer. However, when a separate adhesive layer is actually placed, there are several problems, such as ensuring the amount of skin permeation of the drug sufficient to achieve a desired dosing effect and changes in the physical properties of the adhesive layer due to the drug diffused in the drug layer, and thus, similarly, the attempt is unsatisfactory in providing a long-term sustained release transdermal composition.

Moreover, pressure-sensitive adhesives generally used in patches are required to exhibit adhesiveness to the skin, compatibility with drugs and other excipients, and the like. An acrylic adhesive, such as TRS (Sekisui Chemical Co., Osaka, Japan) or Duro-Tak (Henkel, US), is conventionally used as an adhesive having the above characteristics. However, when such an acrylic adhesive is used as an adhesive matrix for a transdermal composition, drug diffusion in the adhesive layer is slowed down due to the interaction between the drug and acrylic polymers in the adhesive layer, and the migration of the drug from the adhesive layer to the skin is also lowered, leading to a difficulty in delivering a required amount of the drug.

DETAILED DESCRIPTION OF THE INVENTION

Technical Problem

Therefore, the present inventors have prepared a transdermal composition having a special drug-permeable double-layer system. The present inventors have verified that such a transdermal composition achieves a reduction in patch size and thickness which leads to a reduced skin irritation when attached to the skin for a long period of time, contains a high concentration of drug in a hydrophobic matrix so as to enable a long-term administration, and has a significantly improved skin permeation rate compared with existing donepezil patches. As such the present inventors have verified that such a transdermal composition can maintain a valid therapeutic efficacy over a long period of time, and thus have completed the present invention.

Therefore, an aspect of the present invention is to provide a transdermal composition containing donepezil as an active ingredient, the transdermal composition comprising:
(a) a backing layer;
(b) a drug-containing matrix layer comprising, based on a total weight of the drug-containing matrix layer,
 (b-1) 15-55 wt % of donepezil or a pharmaceutically acceptable salt thereof,
 (b-2) 25-70 wt % of an EVA-based adhesive,
 (b-3) 5-20 wt % of at least one selected from the group consisting of a pyrrolidone derivative and a $C_{8-18}$ aliphatic derivative, and
 (b-4) 1-10 wt % of triacetin or a citric acid derivative,
(c) a polymer adhesive matrix layer comprising, based on a total weight of the polymer adhesive matrix layer, 60 wt % or more of an acrylic adhesive; and
(d) a release layer.

Another aspect of the present invention is to provide a method for administering donepezil into a subject, the method comprising:
(1) attaching, to the skin of a subject, a transdermal composition comprising donepezil as an active ingredient, wherein the transdermal composition comprises
(a) a backing layer;
(b) a drug-containing matrix layer comprising, based on a total weight of the drug-containing matrix layer,
 (b-1) 15-55 wt % of donepezil or a pharmaceutically acceptable salt thereof,
 (b-2) 25-70 wt % of an EVA-based adhesive,
 (b-3) 5-20 wt % of at least one selected from the group consisting of a pyrrolidone derivative and a $C_{8-18}$ aliphatic derivative, and
 (b-4) 1-10 wt % of triacetin or a citric acid derivative;
(c) a polymer adhesive matrix layer comprising, based on a total weight of polymer adhesive matrix layer, 60 wt % or more of an acrylic adhesive; and
(d) a release layer; and
(2) maintaining the transdermal composition attached to the skin of the subject for a time sufficient to deliver donepezil to the subject.

Still another aspect of the present invention is to provide a kit comprising a transdermal composition, wherein the transdermal composition comprises:
(a) a backing layer;
(b) a drug-containing matrix layer comprising, based on a total weight of the drug-containing matrix layer,
 (b-1) 15-55 wt % of donepezil or a pharmaceutically acceptable salt thereof,
 (b-2) 25-70 wt % of an EVA-based adhesive,
 (b-3) 5-20 wt % of at least one selected from the group consisting of a pyrrolidone derivative and a $C_{8-18}$ aliphatic derivative, and
 (b-4) 1-10 wt % of triacetin or a citric acid derivative;
(c) a polymer adhesive matrix layer comprising, based on a total weight of polymer adhesive matrix layer, 60 wt % or more of an acrylic adhesive; and
(d) a release layer.

Technical Solution

In accordance with an aspect of the present invention, there is provided a transdermal composition containing donepezil as an active ingredient, the transdermal composition comprising:
(a) a backing layer;
(b) a drug-containing matrix layer comprising, based on a total weight of the drug-containing matrix layer,
(b-1) 15-55 wt % of donepezil or a pharmaceutically acceptable salt thereof,
(b-2) 25-70 wt % of an EVA-based adhesive,
(b-3) 5-20 wt % of at least one selected from the group consisting of a pyrrolidone derivative and a $C_{8-18}$ aliphatic derivative, and
(b-4) 1-10 wt % of triacetin or a citric acid derivative,
(c) a polymer adhesive matrix layer comprising, based on a total weight of the polymer adhesive matrix layer, 60 wt % or more of an acrylic adhesive; and
(d) a release layer.

In accordance with another aspect of the present invention, there is provided a method for administering donepezil into a subject, the method comprising:
(1) attaching, to the skin of a subject, a transdermal composition comprising donepezil as an active ingredient, wherein the transdermal composition comprises
(a) a backing layer;
(b) a drug-containing matrix layer comprising, based on a total weight of the drug-containing matrix layer,
(b-1) 15-55 wt % of donepezil or a pharmaceutically acceptable salt thereof,
(b-2) 25-70 wt % of an EVA-based adhesive,
(b-3) 5-20 wt % of at least one selected from the group consisting of a pyrrolidone derivative and a $C_{8-18}$ aliphatic derivative, and
(b-4) 1-10 wt % of triacetin or a citric acid derivative;
(c) a polymer adhesive matrix layer comprising, based on a total weight of polymer adhesive matrix layer, 60 wt % or more of an acrylic adhesive; and
(d) a release layer; and
(2) maintaining the transdermal composition attached to the skin of the subject for a time sufficient to deliver donepezil to the subject.

In accordance with still another aspect of the present invention, there is provided a kit comprising a transdermal composition, wherein the transdermal composition comprises:
(a) a backing layer;
(b) a drug-containing matrix layer comprising, based on a total weight of the drug-containing matrix layer,
(b-1) 15-55 wt % of donepezil or a pharmaceutically acceptable salt thereof,
(b-2) 25-70 wt % of an EVA-based adhesive,
(b-3) 5-20 wt % of at least one selected from the group consisting of a pyrrolidone derivative and a $C_{8-18}$ aliphatic derivative, and
(b-4) 1-10 wt % of triacetin or a citric acid derivative;
(c) a polymer adhesive matrix layer comprising, based on a total weight of polymer adhesive matrix layer, 60 wt % or more of an acrylic adhesive; and
(d) a release layer.

Figure 1:
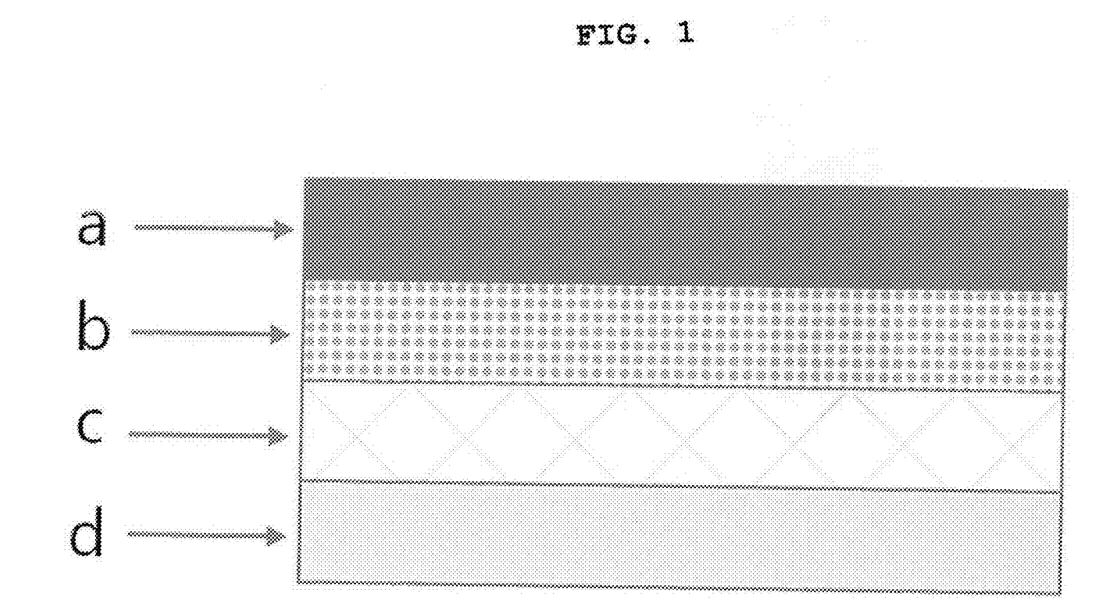
FIG. 1 is a cross-sectional view of a transdermal composition for treating dementia comprising donepezil as an active ingredient according to the present invention (a: a backing layer; b: a drug-containing matrix layer; c: an adhesive matrix layer; d: a release layer).

Hereinafter, the present invention will be described in detail.

The transdermal composition according to the present invention has a backing layer, which is disposed on one surface of a drug-containing matrix layer and is composed of a base material supporting the drug-containing matrix layer, in order to prevent the loss of donepezil from the composition while it is attached to the skin or stored. As the base material constituting the backing layer, a known base material used in a patch or the like may be used. The base material used in the backing layer of the present invention is preferably a material (base material) which is thin and flexible, has no reactivity with the drug-containing matrix layer, causes no allergic reaction due to the absence of reaction with the skin, and does not lead to absorption or diffusion of a drug into the backing layer. Specifically, for the backing layer according to the present invention, a plastic film commonly used in a transdermal composition, such as polyethylene, polypropylene, ethylene vinyl acetate copolymer, vinylon, polyester, polyurethane, nylon, polyacrylonitrile, polyethylene terephthalate, polyolefin, and the like; in order to prevent the separation of the transdermal composition by the moisture evaporating from the human body, a non-woven fabric, such as rayon or polyester, having water absorbing ability; a woven fabric, such as polyester, acrylic, silk, or cotton; or a laminated hybrid material thereof may be used, while any drug protective material (base material) used in a conventional transdermal composition may be used. Preferably, the base material constituting the backing layer of the present invention may be polyester.

The thickness of the backing layer according to the present invention may be 8-100 μm, preferably 10-60 μm.

In the transdermal composition of the present invention, the drug-containing matrix layer is disposed on one surface of the backing layer, and contains donepezil as an active ingredient. The donepezil is an acetylcholine esterase inhibitor, and in the present invention, the donepezil may be used in any form of a donepezil free base or a pharmaceutically acceptable salt thereof. The donepezil free base is represented by chemical formula $C_{24}H_{29}NO_3$, and the IUPAC name thereof is (±)-2,3-dihydro-5,6-dimethoxy-2-[[1-(phenylmethyl)-4-piperidinyl]methyl]-1H-inden-1-one. The donepezil free base may, preferably, have the structure of Chemical Formula 1 below.

<Formula 1>

An acid addition salt formed by a pharmaceutically acceptable free acid is useful as the pharmaceutically acceptable salt of donepezil. An acid addition salt may be obtained from inorganic acids, such as hydrochloric acid, nitric acid, phosphoric acid, sulfuric acid, hydrobromic acid, hydroiodic acid, nitrous acid, and phosphorous acid; and non-toxic organic acids, such as aliphatic mono- and di-carboxylates, phenyl-substituted alkanoates, hydroxy alkanoates and alkanedioates, aromatic acids, aliphatic and aromatic sulfonic acids. The pharmaceutically non-toxic salts include sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, β-hydroxybutylate, glycolate, malate, tartrate, methanesulfonate, propanesulfonate, naphthalene-1-sulfonate, naphthalene-2-sulfonate, and mandelate. Preferably, the donepezil contained in the drug-containing matrix layer of the present invention may be characterized by being in the form of its free base.

In addition, the donepezil is uniformly dispersed in a drug-containing matrix layer, and may be contained in an amount of 15-55 wt % based on the total weight of the drug-containing matrix layer. That is, the donepezil may be contained in an amount of 15-50 wt %, 15-45 wt %, 15-40 wt %, 15-35 wt %, 15-30 wt %, 15-25 wt %, 15-20 wt %, 20-55 wt %, 20-50 wt %, 20-45 wt %, 20-40 wt %, 20-35 wt %, 20-30 wt %, 20-25 wt %, 25-55 wt %, 25-50 wt %, 25-45 wt %, 25-40 wt %, 25-35 wt %, 25-30 wt %, 30-55 wt %, 30-50 wt %, 30-45 wt %, 30-40 wt %, 30-35 wt %, 35-55 wt %, 35-50 wt %, 35-45 wt %, 35-40 wt %, 40-55 wt %, 40-50 wt %, 40-45 wt %, 45-55 wt %, 45-50 wt %, or 50-55 wt %, preferably 26-55 wt %, and most preferably 30-50 wt %.

If the content of donepezil or a pharmaceutically acceptable salt thereof is less than 15 wt %, its drug effect is insufficient, while, if the content thereof is higher than 55 wt %, the content of a polymer base material is small in the composition, failing to attain sufficient hardness. Thus, such a content of donepezil or a pharmaceutically acceptable salt thereof may not be desirable in the preparation of a transdermal composition. In the transdermal composition of the present invention, the donepezil is contained in a supersaturated state in the drug-containing matrix layer, and uniformly-sized donepezil microcrystals are distributed in a uniform density throughout the drug-containing matrix layer.

The drug-containing matrix layer of the present invention is characterized by the use of a polymer base material, along with an EVA adhesive as a pressure-sensitive adhesive. A polyethylene vinyl acetate copolymer, which is a main raw material of the EVA adhesive, has various applications according to the content of vinyl acetate; has excellent weather resistance, aging stability, tearing strength, stress resistance, and ozone resistance; and is a non-toxic thermoplastic elastic resin which is more transparent than rubber. In the present invention, in order to possess a preferable adhesive strength, the vinyl acetate (VA) content of polyethylene vinyl acetate (EVA) used in the EVA adhesive may be contained in a content of 4-50 wt %, and preferably 35-45 wt %.

The content of the EVA adhesive as a polymer base material constituting the drug-containing matrix layer may be contained in an amount of 25-70 wt % based on the total weight of the drug-containing matrix layer. That is, the content of the EVA adhesive may be contained in an amount of 25-70 wt %, 25-65 wt %, 25-60 wt %, 25-55 wt %, 25-50 wt %, 25-45 wt %, 25-40 wt %, 25-35 wt %, 25-30 wt %, 30-70 wt %, 30-65 wt %, 30-60 wt %, 30-55 wt %, 30-50 wt %, 30-45 wt %, 30-40 wt %, 30-35 wt %, 35-70 wt %, 35-65 wt %, 35-60 wt %, 35-55 wt %, 35-50 wt %, 35-45 wt %, 35-40 wt %, 40-70 wt %, 40-65 wt %, 40-60 wt %, 40-55 wt %, 40-50 wt %, 40-45 wt %, 45-70 wt %, 45-65 wt %, 45-60 wt %, 45-55 wt %, 45-50 wt %, 50-70 wt %, 50-65 wt %, 50-60 wt %, 50-55 wt %, 55-70 wt %, 55-65 wt %, 55-60 wt %, 60-70 wt %, 60-65 wt %, or 65-70 wt %, and preferably 30-60 wt %. If the content of the EVA adhesive is outside the above indicated content range, such a content may cause disadvantages in terms of applicability to the skin and compatibility with a drug and other excipients.

For the enhancement of skin permeability of a drug, a pyrrolidone derivative, a $C_{8-18}$ aliphatic derivative, triacetin, and a citric acid derivative may be used as a skin permeation enhancer in their specific combination in the drug-containing matrix layer of the present invention.

Therefore, the drug-containing matrix layer of the present invention contains at least one material selected from the group consisting of a pyrrolidone derivative and a $C_{8-18}$ aliphatic derivative. That is, the drug-containing matrix layer of the present invention contains at least one selected from the group consisting of a pyrrolidone derivative, a $C_{8-18}$ aliphatic derivative, and a mixture thereof.

The kind of the pyrrolidone derivative is not particularly limited as long as it is a known pyrrolidone derivative. For example, the pyrrolidone derivative may be at least one selected from the group consisting of N-cyclohexyl-2-pyrrolidone, 1-butyl-3-dodecyl-2-pyrrolidone, 1,5-dimethyl-2-pyrrolidone, 1-ethyl-2-pyrrolidone, 1-hexyl-4-methyloxycarbonyl-2-pyrrolidone, 1-hexyl-2-pyrrolidone, 1-(2-hydroxyethyl)pyrrolidone, 3-hydroxy-N-methyl-2-pyrrolidone, 1-lauryl-4-methyloxycarbonyl-2-pyrrolidone, N-methyl-2-pyrrolidone, N-caprylyl-2-pyrrolidone, and N-dodecyl-2-pyrrolidone. Preferably, the pyrrolidone derivative may be N-dodecyl-2-pyrrolidone.

The kind of the $C_{8-18}$ aliphatic derivative is not particularly limited as long as it is a known $C_{8-18}$ aliphatic derivative. For example, the $C_{8-18}$ aliphatic derivative may be at least one selected from the group consisting of lauryl alcohol, oleyl alcohol, lauryl lactate, glycerol monolaurate, glycerol monooleate, isopropyl myristate, sorbitan monolaurate, sorbitan monooleate, propylene glycol monolaurate, propylene glycol monooleate, oleyl macrogol glyceride, oleic acid, lauroyl macrogol glyceride, linoleoyl macrogol glyceride, propylene glycol caprylate/caprate, propylene glycol monocaprylate, and sorbitan monostearate. Preferably, the $C_{8-18}$ aliphatic derivative may be glycerol monooleate or isopropyl myristate.

At least one material selected from the group consisting of a pyrrolidone derivative and a $C_{8-18}$ aliphatic derivative may be contained in a content of 5-20 wt % based on the total weight of the drug-containing matrix layer. That is, the material may be contained in a content of 6-20 wt %, 6-19 wt %, 6-18 wt %, 6-17 wt %, 6-16 wt %, 6-15 wt %, 6-14 wt %, 6-13 wt %, 7-20 wt %, 7-19 wt %, 7-18 wt %, 7-17 wt %, 7-16 wt %, 7-15 wt %, 7-14 wt %, 7-13 wt %, 8-20 wt %, 8-19 wt %, 8-18 wt %, 8-17 wt %, 8-16 wt %, 8-15 wt %, 8-14 wt %, 8-13 wt %, 9-20 wt %, 9-19 wt %, 9-18 wt %, 9-17 wt %, 9-16 wt %, 9-15 wt %, 9-14 wt %, 9-13 wt %, and preferably 8-17 wt %. It is desirable to minimize a side effect in the skin by minimizing the use of such a material.

In addition, the drug-containing matrix layer of the present invention contains any one material selected from triacetin or a citric acid derivative. That is, triacetin and a citric acid derivative are not simultaneously contained in a composition in the drug-containing matrix layer of the present invention.

The kind of the citric acid derivative is not particularly limited as long as it is a known citric acid derivative. For example, the citric acid derivative may be at least one selected from the group consisting of acetyl triethyl citrate, diethyl citrate, tributyl citrate, triethyl citrate, and acetyl tributyl citrate. Preferably, the citric acid derivative may be triethyl citrate.

Any one material of triacetin or a citric acid derivative may be contained in an amount of 1-10 wt % based on the total weight of the drug-containing matrix layer. That is, such a material may be contained in a content of 1-10 wt %, 1-9 wt %, 1-8 wt %, 1-7 wt %, 1-6 wt %, 2-10 wt %, 2-9 wt %, 2-8 wt %, 2-7 wt %, 2-6 wt %, 3-10 wt %, 3-9 wt %, 3-8 wt %, 3-7 wt %, 3-6 wt %, 4-10 wt %, 4-9 wt %, 4-8 wt %, 4-7 wt %, or 4-6 wt %, and preferably 3-8 wt %.

That is, for the transdermal composition of the present invention, following exemplary combinations may be used in the present invention: a combination of a pyrrolidone derivative and triacetin; a combination of a $C_{8-18}$ aliphatic derivative and triacetin; a combination of a pyrrolidone derivative and a citric acid derivative; a combination of a $C_{8-18}$ aliphatic derivative and a citric acid derivative; a combination of a pyrrolidone derivative, a $C_{8-18}$ aliphatic derivative, and triacetin; a combination of a pyrrolidone derivative, a $C_{8-18}$ aliphatic derivative, and a citric acid derivative.

Preferably, the drug-containing matrix layer of the present invention may be composed of (b-1) 15-55 wt % of donepezil or a pharmaceutical acceptable salt thereof, (b-2) 25-70 wt % of an EVA-based adhesive, (b-3) 5-20 wt % of a pyrrolidone derivative, and (b-4) 1-10 wt % of triacetin.

In addition, the drug-containing matrix layer of the present invention may be prepared in its thickness of 50-150 μm, and preferably 70-120 μm.

The transdermal composition of the present invention has an adhesive matrix layer, which is disposed on the other surface of the drug-containing matrix layer and brings the transdermal composition into continuous contact with the skin to facilitate the absorption of its active ingredient. As used herein, the term "adhesive matrix layer" is used interchangeably the term "adhesive layer". In the present invention, the adhesive matrix layer is characterized by its functions of controlling a continuous drug release and improving adhesiveness.

In the present invention, the adhesive matrix layer is characterized by containing 60 wt % or more of an acrylic adhesive. For example, the acrylic adhesive may be contained in an amount of 60 wt %, 61 wt %, 62 wt %, 63 wt %, 64 wt %, 65 wt %, 66 wt %, 67 wt %, 68 wt %, 69 wt %, 70 wt %, 71 wt %, 72 wt %, 73 wt %, 74 wt %, 75 wt %, 76 wt %, 77 wt %, 78 wt %, 79 wt %, 80 wt %, 81 wt %, 82 wt %, 83 wt %, 84 wt %, 85 wt %, 86 wt %, 87 wt %, 88 wt %, 89 wt %, 90 wt %, 91 wt %, 92 wt %, 93 wt %, 94 wt %, 95 wt %, 96 wt %, 97 wt %, 98 wt %, 99 wt %, or 100 wt %. Preferably, the acrylic adhesive may be contained in a content of 60-100 wt % based on the total weight of the adhesive matrix layer, and most preferably 80 wt % or more (that is, 80-100 wt %).

Preferably, the acrylic adhesive contained in the adhesive matrix layer of the present invention is an acrylic adhesive containing no functional group. The kind of such a functional group is not particularly limited, while, specifically, functional group such as a hydroxy group, a carboxyl group, an amino group, and a sulfonyl group may not be contained in the acrylic adhesive.

Particularly, as for the acrylic adhesive not containing a functional group according to the present invention, a known commercialized product, for example, Duro-Tak™ 87-9088, Duro-Tak™ 87-900A, Duro-Tak™ 87-901A, Duro-Tak™ 4098, Duro-Tak™ 5298, or Duro-Tak™ 87-9301 may be used, without limitation thereto.

The adhesive matrix layer may further contain a skin permeation enhancer. The kind of the skin permeation enhancer is not particularly limited, while, for example, a pyrrolidone derivative, a $C_{8-18}$ aliphatic derivative, triacetin, a citric acid derivative, and the like may be used. Such a material is as described above. In the present invention, the skin permeation enhancer contained in the adhesive matrix layer may be preferably a $C_{8-18}$ aliphatic derivative, and most preferably may be isopropyl myristate or glycerol monooleate.

The skin permeation enhancer contained in the adhesive matrix layer may be contained as a remaining amount of the acrylic adhesive proportion based on the total weight of the adhesive matrix layer. For example, if the acrylic adhesive is contained in a content of 95 wt % in the adhesive matrix layer, the skin permeation enhancer may be contained in a content of 5 wt %. If the acrylic adhesive is contained in a content of 100%, the skin permeation enhancer is not actually contained. Preferably, the skin permeation enhancer may be contained in a content of 1-40 wt % based on the total weight of the adhesive matrix layer. That is, the skin permeation enhancer may be contained in a content of 1-40 wt %, 1-35 wt %, 1-30 wt %, 1-25 wt %, 1-20 wt %, 1-15 wt %, 1-10 wt %, 1-5 wt %, 5-40 wt %, 5-35 wt %, 5-30 wt %, 5-25 wt %, 5-20 wt %, 5-15 wt %, 5-10 wt %, 10-40 wt %, 10-35 wt %, 10-30 wt %, 10-25 wt %, 10-20 wt %, 10-15 wt %, 15-40 wt %, 15-35 wt %, 15-30 wt %, 15-25 wt %, 15-20 wt %, 20-40 wt %, 20-35 wt %, 20-30 wt %, 20-25 wt %, 25-40 wt %, 25-35 wt %, 25-30 wt %, 30-40 wt %, 30-35 wt %, or 35-40 wt %.

According to an example of the present invention, the skin permeability tended to increase as the content of the skin permeation enhancer was increased in the adhesive layer. When the content of the skin permeation enhancer was low, the effect of enhancing a skin permeation increased linearly. However, when the content of the skin permeation enhancer exceeded about 20 wt %, the effect of enhancing such a skin permeation increased non-linearly. Meanwhile, if the content of the skin permeation enhancer contained in the adhesive matrix layer exceeds 40 wt % based on the total weight of the adhesive matrix layer, such a content is not preferable since it influences the physical properties of the transdermal composition, causing a problem in which residual materials remain when attached to the skin.

The adhesive matrix layer of the present invention does not contain donepezil as an active ingredient.

The adhesive matrix layer may be prepared to have its thickness of 20-70 μm, and preferably 30-60 μm.

The transdermal composition of the present invention comprises a release layer, which is disposed on the other surface of the adhesive matrix layer and is to be removed before the transdermal composition is applied onto the skin. As the release layer, a release film or laminated material thereof conventionally used for a transdermal composition may be used. For example, a film of polyethylene, polyester, polyvinyl chloride, polyvinylidene chloride, or the like, a paper, or a laminated material thereof, which is coated with a silicone resin or a fluorine resin, may be used, without limitation thereto.

The transdermal composition of the present invention exhibits its therapeutic effect via donepezil as an active ingredient. Therefore, the use of the transdermal composition of the present invention is not particularly limited as long as the use of the transdermal composition is for any disease on which donepezil shows its therapeutic efficacy, without limitation thereto. For example, the transdermal composition of the present invention has a therapeutic use for degenerative brain disease, and the degenerative brain disease includes Alzheimer's, dementia, memory damage, and the like, but is not limited thereto.

In addition, the transdermal composition of the present invention is administrable for 1-10 days, and may show an effective therapeutic effect for preferably 3-7 days.

The transdermal composition of the present invention contains, as an active ingredient, donepezil at 1-6 mg/cm$^2$ for the area thereof (that is, for the area of a patch), and preferably 2-5 mg/cm$^2$. If the content of the active ingredient is less than 1 mg/cm$^2$, the drug effect may be insufficient. If the content of the active ingredient is more than 6 mg/cm$^2$, the contents of the polymer base material and the skin permeation enhancer are small and thus undesirable in the preparation of a transdermal composition, since the transdermal composition does not exhibit a sufficient hardness.

With respect to the transdermal composition containing donepezil as an active ingredient according to the present invention, the patch size and thickness are reduced compared with existing donepezil-containing patches, while a high concentration of the drug is contained in a hydrophobic matrix; a drug can be continuously released for a long period of time due to the excellent adhesiveness of the transdermal composition to the skin for a long period of time; and the skin permeability of a drug is excellent so that the blood concentration of the active ingredient reaches a therapeutic concentration of high dynamic equilibrium during the application period without reaching a concentration at which side effects occur, and therefore, the transdermal composition can be favorably used as a substitution for a conventional oral composition for treating dementia.

These features are due to a drug-permeable special double layer system (drug-containing matrix layer and adhesive matrix layer) provided by the present invention, and the long-term dosing effect of the patch of the present invention is remarkably shown due to the special material composition of the double layer, which is disclosed for the first time in the present invention.

The present invention provides a method for administering donepezil into a subject, the method comprising:

(1) attaching, to the skin of a subject, a transdermal composition comprising donepezil as an active ingredient, wherein the transdermal composition comprises:
- (a) a backing layer;
- (b) a drug-containing matrix layer comprising, based on a total weight of the drug-containing matrix layer,
  - (b-1) 15-55 wt % of donepezil or a pharmaceutically acceptable salt thereof,
  - (b-2) 25-70 wt % of an EVA-based adhesive,
  - (b-3) 5-20 wt % of at least one selected from the group consisting of a pyrrolidone derivative and a $C_{8-18}$ aliphatic derivative, and
  - (b-4) 1-10 wt % of triacetin or a citric acid derivative;
- (c) a polymer adhesive matrix layer comprising, based on a total weight of polymer adhesive matrix layer, 60 wt % or more of an acrylic adhesive; and
- (d) a release layer; and (2) maintaining the transdermal composition attached to the skin of the subject for a time sufficient to deliver donepezil to the subject.

The step of attaching to the skin may be attained by removing a release layer of the transdermal composition and contacting the adhesive matrix layer to the skin. In the present invention, the part of the skin to which the transdermal composition is attached is not particularly limited, but may preferably be the back, chest, arms, or the like.

Herein, the term "time sufficient to deliver donepezil to a subject" may be construed to mean a time sufficient for donepezil to reach a blood concentration at which drug efficacy can be exerted. In the present invention, the time sufficient to deliver donepezil to the subject may be 1-10 days, preferably 2-7 days, and most preferably 3-4 days, but is not limited thereto.

The present invention provides A kit comprising a transdermal composition, wherein the transdermal composition comprises:
- (a) a backing layer;
- (b) a drug-containing matrix layer comprising, based on a total weight of the drug-containing matrix layer,
  - (b-1) 15-55 wt % of donepezil or a pharmaceutically acceptable salt thereof,
  - (b-2) 25-70 wt % of an EVA-based adhesive,
  - (b-3) 5-20 wt % of at least one selected from the group consisting of a pyrrolidone derivative and a $C_{8-18}$ aliphatic derivative, and
  - (b-4) 1-10 wt % of triacetin or a citric acid derivative;
- (c) a polymer adhesive matrix layer comprising, based on a total weight of polymer adhesive matrix layer, 60 wt % or more of an acrylic adhesive; and
- (d) a release layer.

Advantageous Effects

The transdermal composition of the present invention contains a high concentration of donepezil in the hydrophobic matrix and has excellent adhesiveness to the skin for a long period of time, so that a drug can be continuously released for a long period of time and the skin permeation rate is remarkably improved compared with an existing donepezil patches. Therefore, the transdermal composition of the present invention can continuously maintain an effective therapeutic effect for a long period of time.

Mode for Carrying Out the Invention

Hereinafter, the present invention will be described in detail.

However, the following examples are merely for illustrating the present invention and are not intended to limit the scope of the present invention.

Examples 1 to 8 and Comparative Examples 1 to 4

Preparation of Transdermal Composition Containing Donepezil

Example 1

Methylene chloride was added to 55 wt % of donepezil, 5 wt % of triacetin, 10 wt % of N-dodecyl-2-pyrrolidone, and 30 wt % of an EVA adhesive to obtain a solid content of 40%, which was then completely dissolved, thereby preparing the drug-containing adhesive solution. The drug-containing adhesive solution was coated on a silicone-treated polyester release film fixed on an applicator, and dried at 70° C. for 10 minutes at an air speed of 1300 rpm to prepare a sheet of a drug-containing matrix layer having a thickness of 70 μm, which was then bound to a polyester backing film (corresponding to a backing layer), thereby preparing a drug-containing matrix layer. In addition, an acrylic adhesive (Duro-Tak™ 87-9301) having a solid content of 35-42% was coated on a silicone-treated polyester release film and dried at 100° C. for 10 minutes at an air speed of 1300 rpm, thereby preparing an adhesive matrix layer with a thickness of 50 μm. Thereafter, the release film of the drug-containing matrix layer was removed and then bound to the adhesive matrix layer. After the binding, the resulting product was cut into a size of 50 cm$^2$ to complete a transdermal composition.

Examples 2 to 9 and Comparative Examples 1 to 2

Examples 2 to 9 and Comparative Examples 1 to 2 were prepared by the same method as described in Example except that each composition varied. Table 1 below shows the compositions of Examples 2 to 9 and Comparative Examples 1 and 2.

Comparative Example 3

Toluene was added to 13 wt % of donepezil, 10 wt % of N-dodecyl-2-pyrrolidone, 5 wt % of triacetin, and 72 wt % of an EVA adhesive to obtain a solid content of 40%, which was then completely dissolved. Thereafter, the drug-containing adhesive solution was coated on a silicone-treated polyester release film fixed on the applicator and dried at 90° C. for 10 minutes at an air speed of 1300 rpm to prepare an adhesive layer sheet with a thickness of 85 μm, which was then bound to a polyester backing film, followed by cutting into a size of 50 cm² to complete a transdermal composition.

Comparative Example 4

Comparative Example 4 was prepared by the same method as described in Comparative Example 3 except that the composition was changed. Table 1 below shows the composition of Comparative Example 4.

Example 10

In Example 10, a drug-containing matrix layer was prepared by preparing an adhesive solution containing a drug, which has the same composition as in Example 4, and then performing drying by the same method as described in Example 1. In addition, ethyl acetate was added to 95 wt % of an acrylic adhesive (Duro-Tak™ 87-9301) having a solid content of 35-42% and 5 wt % of isopropyl myristate to obtain a solid content of 35%, which was then completely dissolved. Thereafter, the solution was coated on a silicone-treated polyester release film and dried at 100° C. for 10 minutes at an air speed of 1300 rpm, thereby preparing an adhesive matrix layer with a thickness of 50 μm. Then, the release film of the drug-containing matrix layer was removed, followed by being bound to the adhesive matrix layer. After the binding, the resulting product was cut into a size of 50 cm² to complete a transdermal composition.

Examples 11 to 19 and Comparative Examples 5 to 12

The transdermal compositions in Examples 11 to 19 and Comparative Examples 5 to 12 were prepared by the same method as described in Example 10 except that each composition varied. Table 2 below shows the compositions of adhesive layers in Examples 11 to 19 and Comparative Examples 5 to 12.

TABLE 1

Table of composition of Examples 1 to 9 and Comparative Examples 1 to 4

| | | Drug stroge layer | | | | | | | Adhesive layer | |
|---|---|---|---|---|---|---|---|---|---|---|
| | | Donepezil | EVA adhesive | TA | TC | NP | IPM | GML | Acrylic adhesive | IPM |
| double layer | Example 1 | 55 | 30 | 5 | | 10 | | | 100 | |
| | Example 2 | 50 | 35 | 5 | | 10 | | | 100 | |
| | Example 3 | 40 | 45 | 5 | | 10 | | | 100 | |
| | Example 4 | 30 | 55 | 5 | | 10 | | | 100 | |
| | Example 5 | 20 | 65 | 5 | | 10 | | | 100 | |
| | Example 6 | 15 | 70 | 5 | | 10 | | | 100 | |
| | Example 7 | 30 | 55 | 3 | | 12 | | | 100 | |
| | Example 8 | 30 | 55 | 5 | | | 10 | | 100 | |
| | Example 9 | 30 | 55 | | 5 | 10 | | | 100 | |
| | Comparative Example 1 | 45 | 45 | | | 10 | | | 100 | |
| | Comparative Example 2 | 45 | 45 | | | | | 10 | 100 | |
| mono layer | Comparative Example 3 | 13 | 72 | 5 | | 10 | | | | |
| | Comparative Example 4 | 13 | 72 | 5 | | | 10 | | | |

EVA adhesive: polyethylene vinyl acetate adhesive,
TA: triacetin,
TC: triethyl citrate,
NP: N-dodecyl-2-pyrrolidone,
IPM: isopropyl myristate,
GML: glycerol monolaurate,
acrylic adhesive: polyacrylate adhesive

TABLE 2

Table of composition of Examples 10 to 19 and Compartive Examples 5 to 12

| | | Adhesive layer | | | | | | | | | |
|---|---|---|---|---|---|---|---|---|---|---|---|
| | | Acrylic adhesive | IPM | GMO | NP | TA | TC | PGML | SMO | SML | PML | GML |
| double layer | Example 4 | 100 | | | | | | | | | | |
| | Example 10 | 95 | 5 | | | | | | | | | |

TABLE 2-continued

Table of composition of Examples 10 to 19 and Compartive Examples 5 to 12

| | Adhesive layer | | | | | | | | | | |
|---|---|---|---|---|---|---|---|---|---|---|---|
| | Acrylic adhesive | IPM | GMO | NP | TA | TC | PGML | SMO | SML | PML | GML |
| Example 11 | 90 | 10 | | | | | | | | | |
| Example 12 | 80 | 20 | | | | | | | | | |
| Example 13 | 70 | 30 | | | | | | | | | |
| Example 14 | 60 | 40 | | | | | | | | | |
| Example 15 | 95 | | 5 | | | | | | | | |
| Example 16 | 90 | | 10 | | | | | | | | |
| Example 17 | 80 | | 20 | | | | | | | | |
| Example 18 | 70 | | 30 | | | | | | | | |
| Example 19 | 60 | | 40 | | | | | | | | |
| Comparative Example 5 | 90 | | | 10 | | | | | | | |
| Comparative Example 6 | 90 | | | | 10 | | | | | | |
| Comparative Example 7 | 90 | | | | | 10 | | | | | |
| Comparative Example 8 | 90 | | | | | | 10 | | | | |
| Comparative Example 9 | 90 | | | | | | | 10 | | | |
| Comparative Example 10 | 90 | | | | | | | | 10 | | |
| Comparative Example 11 | 90 | | | | | | | | | 10 | |
| Comparative Example 12 | 90 | | | | | | | | | | 10 |

EVA adhesive: polyethylene vinyl acetate adhesive,
TA: triacetin,
NP: N-dodecyl-2-pyrrolidone,
Acryte adhesive: polyacrylate adhesive,
IPM: isopropyl myristrate,
GMO: glycerol monoolate,
TC: triethyl citrate,
PGML: propylene glycol monolaurate,
SMO: sorbitan monooleate,
SML: sorbitan monolaurate,
PML: polyoxyethylene monolaurate,
GML: glycerol monolaurate

Test Example 1: Evaluation of Drug Skin Permeation of Transdermal Compositions A donepezil skin permeation test was conducted on the patches prepared in Examples 1 to 9 and Comparative Examples 1 to 4 as follows.

The aqueous phase of a diffusion device for a drug permeation test (Franz cell) was prepared by adding 0.1 wt % of sodium azide to a phosphate buffer of pH 7.4 to prevent the skin from decaying. The temperature was kept at 32±0.5° C. by charging the aqueous phase in the diffusion test device (Franz cell), while the human cadaver skin was used. The patches prepared in the Examples and Comparative Examples were cut according to the size of donor cells and then applied to the skin. As time elapsed, the drug-diffused buffer was taken at 500 µl every hour to quantify the amount of the drug that had permeated. HPLC (Agilent 1100 series HPLC) was used for analysis. For analytical conditions, a 40:60 (volume ratio) mixture liquid of acetonitrile and a mixture solution of potassium dihydrogen phosphate buffer, methanol, and triethylamine (the mixture solution being prepared by mixing a 0.02 mol/L potassium dihydrogen phosphate buffer with methanol and triethyl amine at a ratio of 50:50:1 (volume ratio)) was used as a mobile phase; the sample injection amount was 20 µL; the flow rate was 1.0 ml/min; the detection wavelength was 268 nm; and the C18 reverse-phase column was used as a column. Table 3 shows the cumulative drug permeation amount and the skin permeation rate at 3 days after drug permeation in the patches prepared in Examples and Comparative Examples.

TABLE 3

Accumulative amount of permeation and skin permeation rate of transdermal absorption preparation (1)

| | | Accumulative amount of permeation (ug/cm$^2$) | Skin permeation rate (ug/cm$^2$/hr) |
|---|---|---|---|
| double layer | Example 1 | 502.16 ± 46.01 | 6.97 ± 0.64 |
| | Example 2 | 494.51 ± 18.09 | 6.87 ± 0.25 |
| | Example 3 | 391.93 ± 12.96 | 5.44 ± 0.18 |
| | Example 4 | 323.91 ± 2.53 | 4.50 ± 0.04 |
| | Example 5 | 228.52 ± 4.48 | 3.17 ± 0.06 |
| | Example 6 | 153.29 ± 8.6 | 2.13 ± 0.12 |
| | Example 7 | 367.31 ± 12.24 | 5.10 ± 0.17 |
| | Example 8 | 286.02 ± 10.79 | 3.97 ± 0.15 |
| | Example 9 | 299.31 ± 23.27 | 4.16 ± 0.32 |
| | Comparative Example 1 | 184.93 ± 9.26 | 2.57 ± 0.13 |
| | Comparative Example 2 | 167.72 ± 7.37 | 2.33 ± 0.10 |
| mono layer | Comparative Example 3 | 245.64 ± 8.49 | 3.41 ± 0.12 |
| | Comparative Example 4 | 229.87 ± 3.42 | 3.19 ± 0.05 |

From the comparison between the Examples and comparative Examples 3 and 4 in table 3, it can be seen that the monolayer donepezil patches showed high skin permeability in consideration of the drug content. This is because the drug penetrates directly through the adhesive layer. However, when actually applied to the skin, the monolayer composition has low adhesiveness, and thus is not suitable as a long-term attachment type patch. However, the transdermal compositions of the present invention as shown in Examples 1 to 8 were very suitable as a long-term drug release-type transdermal composition due to the excellent adhesive strength of the adhesive matrix layer (adhesive layer), even when applied to the actual skin.

Further, from the comparison between the Examples and Comparative Examples 1 and 2 in Table 3, it can be seen that the composite use of skin permeation enhancers in a specific combination was more effective than the singular use of a skin permeation enhancer. In particular, the composite use of triacetin and N-dodecyl-2-pyrrolidone, the composite use of triacetin and isopropyl myristate, or the composite use of triethyl citrate and N-dodecyl-2-pyrrolidone was found effective.

In addition, in the case of 5 mg of an oral composition, the maximal blood concentration was 9.8±1.1 ng/ml when administered orally once. The oral composition reached a steady state within 15 days after repeated administration, and at the steady state, the mean plasma concentration was 26.5±3.9 ng/ml and the mean plasma clearance was constant at 0.13 L/hr/kg. Through the above data, the required skin permeation rate was found to be approximately 4.134 µg/cm$^2$/hr. It can be seen that, when compared with the Examples in Table 2, the skin permeation rates were maintained similar to or slightly higher than the required skin permeation rate. In addition, it can be seen that, in the skin permeation test of the Examples, the drug was continuously released during the test period. In addition, due to the characteristics of donepezil, the drug has a long half-life (58-90 hr) and high bioavailability (96-100%), and thus, the drug is accumulated in the body for administration for a long period of time, and reaches a therapeutic concentration of a dynamic equilibrium state, and thus exhibits persistency of treatment. Therefore, the transdermal composition of the present invention can sufficiently obtain a therapeutic effect for a long period of time even with one application, and can solve the inconvenience of the required daily administration to the patient.

Test Example 2: Evaluation of Efficacy of Transdermal Composition According to Functional Group Contained in Adhesive Layer Transdermal compositions containing donepezil were prepared using DURO-TAK 87-900A, DURO-TAK 87-9301, and DURO-TAK 87-4098 as acrylic adhesives without a functional group, DURO-TAK 87-2516 as an acrylic adhesive containing a hydroxyl group, DURO-TAK 87-503A and DURO-TAK 87-504A as acrylic adhesives which are acrylate-rubber hybrids, and DURO-TAK 87-2852 as an acrylic adhesive containing a carboxyl group. All the other details (the types and contents of components constituting the backing layer, drug-containing matrix layer, and release layer, and the content of the acrylic adhesive contained in the adhesive layer), other than the type of the acrylic adhesive, were identical to those in Example 3. The prepared transdermal compositions were measured for the amount of skin permeation by the same method as in Test Example 1.

Figure 2:
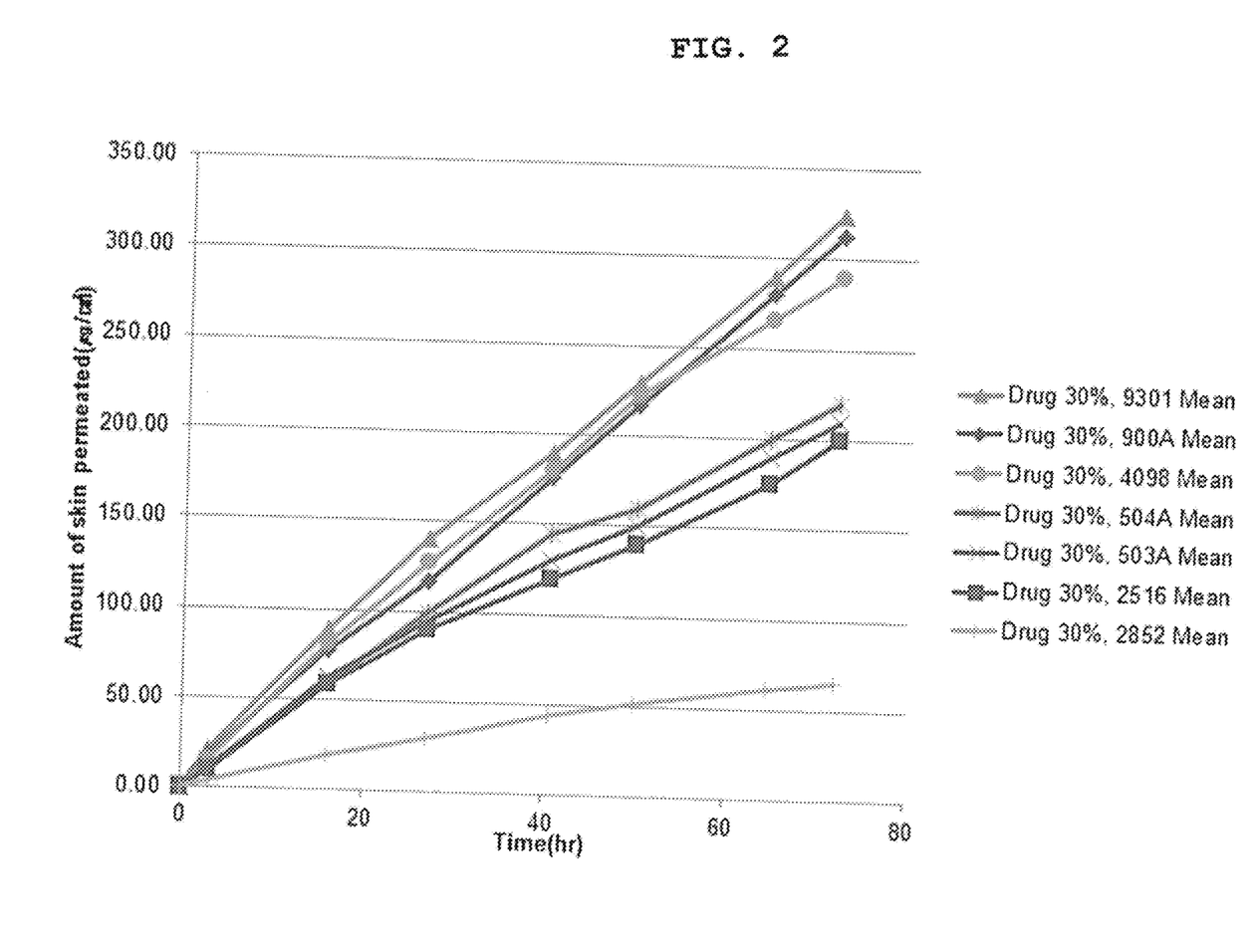
FIG. 2 is a graph showing the results of the amount of the skin permeation of transdermal compositions which were prepared using various types of acrylic adhesives having no functional group or having different functional groups.

As a result, it was verified as shown in FIG. 2 that the transdermal compositions prepared using DURO-TAK 87-900A, DURO-TAK 87-9301, and DURO-TAK 87-4098, which are acrylic adhesives having no functional group, respectively, showed significantly high drug permeation rates.

Test Example 3: Evaluation of Efficacy of Transdermal Composition According to Skin Permeation Enhancer Contained in Adhesive Layer Transdermal compositions were prepared using adhesive layers according to the compositions in Table 2, while all the details (the types and contents of ingredients constituting the backing layer, the drug-containing matrix layer, and the release layer) other than the adhesive layer were identical to those in Example 4. The prepared transdermal compositions were measured for the amount of skin permeation by the same method as in Test Example 1.

TABLE 4

| | | Accumulative amount of permeation (ug/cm$^2$) | Skin permeation rate (ug/cm$^2$/hr) |
|---|---|---|---|
| double layer | Example 4 | 323.91 ± 2.53 | 4.50 ± 0.04 |
| | Example 10 | 391.12 ± 4.55 | 5.43 ± 0.06 |
| | Example 11 | 413.46 ± 13.46 | 5.74 ± 0.19 |
| | Example 12 | 429.34 ± 23.16 | 5.96 ± 0.32 |
| | Example 13 | 437.19 ± 30.35 | 6.07 ± 0.42 |
| | Example 14 | 444.79 ± 36.74 | 6.18 ± 0.51 |
| | Example 15 | 387.34 ± 6.42 | 5.39 ± 0.09 |
| | Example 16 | 421.56 ± 8.44 | 5.86 ± 0.12 |
| | Example 17 | 440.97 ± 21.84 | 6.12 ± 0.30 |
| | Example 18 | 449.17 ± 35.64 | 6.24 ± 0.50 |
| | Example 19 | 452.46 ± 30.28 | 6.28 ± 0.42 |
| | Comparative Example 5 | 411.94 ± 13.07 | 5.72 ± 0.18 |
| | Comparative Example 6 | 347.94 ± 7.5 | 4.83 ± 0.10 |
| | Comparative Example 7 | 340.19 ± 13.01 | 4.72 ± 0.18 |
| | Comparative Example 8 | 396.49 ± 21.13 | 5.51 ± 0.29 |
| | Comparative Example 9 | 381.65 ± 5.03 | 5.30 ± 0.07 |
| | Comparative Example 10 | 374.4 ± 13.5 | 5.20 ± 0.19 |
| | Comparative Example 11 | 384.49 ± 17.26 | 5.34 ± 0.24 |
| | Comparative Example 12 | 406.1 ± 16.21 | 5.64 ± 0.23 |

As a result, it was verified, as shown in Table 4, that, when comparing Examples 10 to 19 and Comparative Examples 5 to 12, which are transdermal compositions containing a skin permeation enhancer in the adhesive layer, with Example 4 which is a transdermal composition not containing a skin permeation enhancer in the adhesive layer, the drug permeation rates were remarkably high when a skin permeation enhancer was contained in the adhesive layer.

In addition, as in Test Example 1, as the content of the skin permeation enhancer increased in the adhesive layer, the skin permeability tended to increase. However, when the content of the skin permeation enhancer was low, the skin permeation enhancement effect increased linearly. However, when the amount of the skin permeation enhancer exceeded a specific content of about 20%, the skin permeation enhancement effect increased nonlinearly. Also, a problem occurred which a higher content of the skin permeation enhancer influenced the physical properties of the transdermal composition, and thus, residues were left when the transdermal composition was attached to the skin.

In addition, all the skin permeation enhancers used in Comparative Examples 5 to 12 had increased skin permeability, but showed lower drug permeation rates or exerted greater influences on the physical properties of the transdermal permeation composition, compared with Examples 10 to 19, and thus, more residues were left when attached to the skin than the Examples.

INDUSTRIAL APPLICABILITY

As set forth above, the present invention is directed to a transdermal composition containing donepezil as an active ingredient and, more specifically, to a transdermal composition containing donepezil as an active ingredient, the transdermal composition comprising: (a) a backing layer; (b) a drug-containing matrix layer comprising, based on a total weight of a drug-containing matrix layer, (b-1) 15-55 wt % of donepezil or a pharmaceutically acceptable salt thereof, (b-2) 25-70 wt % of an EVA-based adhesive, (b-3) 5-20 wt % of at least one selected from the group consisting of a pyrrolidone derivative and a $C_{8-18}$ aliphatic derivative, and (b-4) 1-10 wt % of triacetin or a citric acid derivative, (c) a polymer adhesive matrix layer comprising, based on a total weight of the polymer adhesive matrix layer, 60 wt % or more of an acrylic adhesive; and (d) a release layer.

The transdermal composition of the present invention contains a high concentration of donepezil in the hydrophobic matrix and has excellent adhesiveness to the skin for a long period of time, so that a drug can be continuously released for a long period of time and the skin permeation rate can be remarkably improved compared with existing donepezil patches, and therefore, the transdermal composition of the present invention can continuously maintain an effective therapeutic effect for a long period of time. Accordingly, the transdermal composition of the present invention is highly industrially applicable.

What is claimed is:

1. A transdermal composition containing donepezil as an active ingredient, the transdermal composition comprising:
   (a) a backing layer;
   (b) a drug-containing matrix layer comprising, based on a total weight of the drug-containing matrix layer,
      (b-1) 15-55 wt % of donepezil or a pharmaceutically acceptable salt thereof,
      (b-2) 25-70 wt % of an EVA-based adhesive,
      (b-3) 5-20 wt % of at least one selected from the group consisting of a pyrrolidone derivative and a $C_{8-18}$ aliphatic derivative, and
      (b-4) 1-10 wt % of triacetin or a citric acid derivative,
   (c) a polymer adhesive matrix layer comprising, based on a total weight of the polymer adhesive matrix layer, 60 wt % or more of an acrylic adhesive, wherein the acrylic adhesive does not contain a functional group; and
   (d) a release layer;
   wherein the EVA-based adhesive is an ethylene vinyl acetate (EVA) copolymer; and
   wherein the polymer adhesive matrix layer excludes donepezil or a pharmaceutically acceptable salt thereof.

2. The transdermal composition of claim 1, wherein the donepezil is in a form of a free base.

3. The transdermal composition of claim 1, wherein the donepezil is contained in an amount of 26-55 wt % based on a total weight of the drug-containing matrix layer.

4. The transdermal composition of claim 1, wherein the adhesive matrix layer further comprises a skin permeation enhancer.

5. The transdermal composition of claim 4, wherein the skin permeation enhancer is at least one material selected from the group consisting of a pyrrolidone derivative, a $C_{8-18}$ aliphatic derivative, a citric acid derivative, and triacetin.

6. The transdermal composition of claim 1, wherein the pyrrolidone derivative is at least one selected from the group consisting of N-cyclohexyl-2-pyrrolidone, 1-butyl-3-dodecyl-2-pyrrolidone, 1,5-dimethyl-2-pyrrolidone, 1-ethyl-2-pyrrolidone, 1-hexyl-4-methyloxycarbonyl-2-pyrrolidone, 1-hexyl-2-pyrrolidone, 1-(2-hydroxyethyl)pyrrolidone, 3-hydroxy-N-methyl-2-pyrrolidone, 1-lauryl-4-methyloxycarbonyl-2-pyrrolidone, N-methyl-2-pyrrolidone, N-caprylyl-2-pyrrolidone, and N-dodecyl-2-pyrrolidone.

7. The transdermal composition of claim 6, wherein the pyrrolidone derivative is N-dodecyl-2-pyrrolidone.

8. The transdermal composition of claim 1, wherein the $C_{8-18}$ aliphatic derivative is at least one selected from the group consisting of lauryl alcohol, oleyl alcohol, lauryl lactate, glycerol monolaurate, glycerol monooleate, isopropyl myristate, sorbitan monolaurate, sorbitan monooleate, propylene glycol monolaurate, propylene glycol monooleate, oleyl macrogol glyceride, oleic acid, lauroyl macrogol glyceride, linoleoyl macrogol glyceride, propylene glycol caprylate/caprate, propylene glycol monocaprylate, and sorbitan monostearate.

9. The transdermal composition of claim 8, wherein the aliphatic derivative is glycerol monooleate or isopropyl myristate.

10. The transdermal composition of claim 1, wherein the citric acid derivative is at least one selected from the group consisting of acetyl triethyl citrate, diethyl citrate, tributyl citrate, triethyl citrate, and acetyl tributyl citrate.

11. The transdermal composition of claim 10, wherein the citric acid derivative is triethyl citrate.

12. The transdermal composition of claim 1, wherein the content of vinyl acetate (VA) used in the EVA adhesive is 4-50 wt %.

13. The transdermal composition of claim 1, wherein the content of vinyl acetate (VA) used in the EVA adhesive is 35-45 wt %.

14. A method for administering donepezil into a subject, the method comprising:
   (1) attaching, to the skin of a subject, a transdermal composition comprising donepezil as an active ingredient, wherein the transdermal composition comprises:
      (a) a backing layer;
      (b) a drug-containing matrix layer comprising, based on a total weight of the drug-containing matrix layer,
         (b-1) 15-55 wt % of donepezil or a pharmaceutically acceptable salt thereof,
         (b-2) 25-70 wt % of an EVA-based adhesive,
         (b-3) 5-20 wt % of at least one selected from the group consisting of a pyrrolidone derivative and a $C_{8-18}$ aliphatic derivative, and
         (b-4) 1-10 wt % of triacetin or a citric acid derivative;
      (c) a polymer adhesive matrix layer comprising, based on a total weight of polymer adhesive matrix layer, 60 wt % or more of an acrylic adhesive, wherein the acrylic adhesive does not contain a functional group; and
      (d) a release layer; and
   (2) maintaining the transdermal composition attached to the skin of the subject for a time sufficient to deliver donepezil to the subject;
   wherein the EVA-based adhesive is an ethylene vinyl acetate (EVA) copolymer; and
   wherein the polymer adhesive matrix layer excludes donepezil or a pharmaceutically acceptable salt thereof.

15. The method of claim 14, wherein the time is 1 to 10 days.

16. A kit comprising a transdermal composition, wherein the transdermal composition comprises:
(a) a backing layer;
(b) a drug-containing matrix layer comprising, based on a total weight of the drug-containing matrix layer,
(b-1) 15-55 wt % of donepezil or a pharmaceutically acceptable salt thereof,
(b-2) 25-70 wt % of an EVA-based adhesive,
(b-3) 5-20 wt % of at least one selected from the group consisting of a pyrrolidone derivative and a $C_{8-18}$ aliphatic derivative, and
(b-4) 1-10 wt % of triacetin or a citric acid derivative;
(c) a polymer adhesive matrix layer comprising, based on a total weight of polymer adhesive matrix layer, 60 wt % or more of an acrylic adhesive, wherein the acrylic adhesive does not contain a functional group; and
(d) a release layer;
wherein the EVA-based adhesive is an ethylene vinyl acetate (EVA) copolymer; and
wherein the polymer adhesive matrix layer excludes donepezil or a pharmaceutically acceptable salt thereof.

17. The transdermal composition of claim 4, wherein the adhesive matrix layer comprises a skin permeation enhancer selected from isopropyl myristate or glycerol monooleate.

18. The transdermal composition of claim 1, wherein the composition consists essentially of:
(a) a backing layer;
(b) a drug-containing matrix layer comprising, based on a total weight of the drug-containing matrix layer,
(b-1) 15-55 wt % of donepezil or a pharmaceutically acceptable salt thereof,
(b-2) 25-70 wt % of an EVA-based adhesive,
(b-3) 5-20 wt % of at least one selected from the group consisting of a pyrrolidone derivative and a $C_{8-18}$ aliphatic derivative, and
(b-4) 1-10 wt % of triacetin or a citric acid derivative,
(c) a polymer adhesive matrix layer comprising, based on a total weight of the polymer adhesive matrix layer, 60 wt % or more of an acrylic adhesive, wherein the acrylic adhesive does not contain a functional group; and
(d) a release layer;
wherein the EVA-based adhesive is an ethylene vinyl acetate (EVA) copolymer; and
wherein the polymer adhesive matrix layer excludes donepezil or a pharmaceutically acceptable salt thereof.

19. The transdermal composition of claim 1, wherein the transdermal composition consists of:
(a) a backing layer;
(b) a drug-containing matrix layer comprising, based on a total weight of the drug-containing matrix layer,
(b-1) 15-55 wt % of donepezil or a pharmaceutically acceptable salt thereof,
(b-2) 25-70 wt % of an EVA-based adhesive,
(b-3) 5-20 wt % of at least one selected from the group consisting of a pyrrolidone derivative and a $C_{8-18}$ aliphatic derivative, and
(b-4) 1-10 wt % of triacetin or a citric acid derivative,
(c) a polymer adhesive matrix layer comprising, based on a total weight of the polymer adhesive matrix layer, 60 wt % or more of an acrylic adhesive, wherein the acrylic adhesive does not contain a functional group; and
(d) a release layer;
wherein the EVA-based adhesive is an ethylene vinyl acetate (EVA) copolymer; and
wherein the polymer adhesive matrix layer excludes donepezil or a pharmaceutically acceptable salt thereof.

* * * * *